US008758543B2

(12) United States Patent
Yagyu et al.

(10) Patent No.: US 8,758,543 B2
(45) Date of Patent: Jun. 24, 2014

(54) DISPOSABLE ABSORBENT ARTICLE AND METHOD OF MANUFACTURING THE SAME

(75) Inventors: Kiyoshi Yagyu, Mima-gun (JP); Masaru Fujioka, Mima-gun (JP)

(73) Assignee: Livedo Corporation, Ehime (JP)

( * ) Notice: Subject to any disclaimer, the term of this patent is extended or adjusted under 35 U.S.C. 154(b) by 984 days.

(21) Appl. No.: 12/653,491

(22) Filed: Dec. 15, 2009

(65) Prior Publication Data

US 2010/0107396 A1 May 6, 2010

(30) Foreign Application Priority Data

Mar. 30, 2006 (JP) ................. 2006-094251

(51) Int. Cl.
*B32B 37/00* (2006.01)
*B32B 37/02* (2006.01)
*B32B 38/00* (2006.01)
*B32B 38/04* (2006.01)
*B32B 38/10* (2006.01)

(52) U.S. Cl.
USPC ........... 156/253; 156/250; 156/252; 156/256; 156/257

(58) Field of Classification Search
USPC .................. 156/250, 252, 253, 256, 257
See application file for complete search history.

(56) References Cited

U.S. PATENT DOCUMENTS

| 4,855,558 A | 8/1989 | Ramsbro |
| 5,147,487 A | 9/1992 | Nomura et al. |
| 5,622,581 A * | 4/1997 | Ducker et al. ............... 156/163 |
| 5,634,757 A | 6/1997 | Schanz |
| 5,658,639 A | 8/1997 | Curro et al. |
| 6,089,557 A | 7/2000 | Obrist |
| 6,152,436 A | 11/2000 | Sonderegger et al. |
| 6,367,814 B1 | 4/2002 | Luescher et al. |
| 6,395,957 B1 | 5/2002 | Chen et al. |
| 6,527,266 B1 | 3/2003 | Yonezawa et al. |
| 6,613,954 B1 | 9/2003 | Horney et al. |
| 2001/0029141 A1 | 10/2001 | Mizutani et al. |
| 2003/0021951 A1 | 1/2003 | Desai et al. |
| 2004/0133180 A1* | 7/2004 | Mori et al. ............... 604/385.25 |
| 2005/0158513 A1 | 7/2005 | Peacock et al. |
| 2005/0256488 A1 | 11/2005 | Sperl |
| 2006/0107505 A1 | 5/2006 | Desai et al. |
| 2006/0254708 A1* | 11/2006 | Wada et al. .................. 156/259 |

FOREIGN PATENT DOCUMENTS

| EP | 0 806 928 | 1/1996 |
| EP | 1 155 668 | 5/2001 |
| EP | 1 179 330 | 6/2001 |
| EP | 1 374 814 | 3/2002 |
| EP | 1 300 124 | 9/2002 |
| EP | 1 787 610 | 6/2005 |
| GB | 441 347 | 1/1936 |
| JP | 7-163617 | 6/1995 |
| JP | 10-058258 | 3/1998 |
| JP | 10-085257 | 4/1998 |
| JP | 2001-038562 | 2/2001 |
| JP | 2001-038564 | 2/2001 |

(Continued)

*Primary Examiner* — Philip Tucker
*Assistant Examiner* — Christopher C Caillouet
(74) *Attorney, Agent, or Firm* — Jordan and Hamburg LLP

(57) ABSTRACT

A disposable absorbent article comprises an outer cover, and an absorbent member attached to the skin facing side of the outer cover. The absorbent member includes an absorber. At least a crotch zone of the outer cover is subjected to a softening process for softening a material of the outer cover.

2 Claims, 4 Drawing Sheets

(56) References Cited

FOREIGN PATENT DOCUMENTS

| | | |
|---|---|---|
| JP | 2001-328191 | 11/2001 |
| JP | 2001-521590 | 11/2001 |
| JP | 2002-178428 | 6/2002 |
| JP | 2002-253605 | 9/2002 |
| JP | 2003-102783 | 4/2003 |
| JP | 2004-154250 | 6/2004 |
| WO | WO-96/00551 | 1/1996 |
| WO | WO-97/11661 | 4/1997 |
| WO | WO-01/80800 | 11/2001 |
| WO | WO-02/34181 | 5/2002 |
| WO | WO-03/008688 | 1/2003 |
| WO | WO-2005/110319 | 11/2005 |
| WO | WO-2006/004002 | 1/2006 |

\* cited by examiner

DISPOSABLE ABSORBENT ARTICLE AND METHOD OF MANUFACTURING THE SAME

This is a Divisional Application of U.S. Ser. No. 11/711,425 filed Feb. 26, 2007, now abandoned.

BACKGROUND OF THE INVENTION

1. Field of the Invention

The present invention relates to a disposable absorbent article and a method of manufacturing the same.

2. Description of the Background Art

A disposable absorbent article made of a material having poor flexibility is less likely to fit the shape of wearer's body and causes rough and uncomfortable feeling to the wearer's skin. Ensuring material flexibility is therefore an important issue. Particularly, the crotch zone of an absorbent article undergoes great changes in shape and the like before and after putting on the article, and further, includes an absorber that is likely to mainly cause the rough feeling. Therefore, ensuring the flexibility of the crotch zone is of particular importance.

Conventional disposable absorbent articles, however, do not take sufficient measures to ensure the flexibility of the crotch zone and the like.

SUMMARY OF THE INVENTION

The present invention has an object to provide a disposable absorbent article with improved flexibility at least in the crotch zone of an outer cover, and a method of manufacturing the same.

A first aspect of a disposable absorbent article according to the present invention comprises: an outer cover; and an absorbent member attached to the skin facing side of the outer cover, the absorbent member including an absorber. At least a crotch zone of the outer cover is subjected to a softening process for softening a material of the outer cover.

The softening process improves the flexibility of at least the crotch zone of the outer cover, which prevents particularly the crotch zone of the absorbent article from being less likely to fit the wearer's body and causing rough and uncomfortable feeling to the wearer's skin.

In a second aspect of the disposable absorbent article, in the disposable absorbent article according to the first aspect, a plurality of almost slit-like holes extending through the outer cover are provided in a portion of the outer cover having been subjected to the softening process.

The plurality of almost slit-like holes extending through the outer cover are created by the softening process. This effectively ensures the flexibility of material for the outer cover and achieves a high degree of breathability of material, thereby avoiding dampness.

In a third aspect of the disposable absorbent article, in the disposable absorbent article according to the first or second aspect, a portion of the outer cover subjected to the softening process is softened by application of blades of a cutter.

The softening process is achieved by applying the blades of the cutter, which effectively improves the flexibility of material with simple processing.

In a fourth aspect of the disposable absorbent article, the disposable absorbent article according to any one of the first to third aspects further comprises elastic members attached from along leg-side edges of the outer cover surrounding the wearer's left and right legs to the crotch zone. Part of the elastic members attached to the crotch zone is cut short to be weakened.

Part of the elastic members positioned in the crotch zone is weakened, which prevents the absorber from receiving an unnecessary force caused by the contractive forces of the elastic members and degrading in its absorptive function.

Further, the elastic members are attached continuously from along the left and right leg-side edges of the outer cover to the crotch zone, and part of the elastic members positioned in the crotch zone is weakened along with the softening process performed on the crotch zone of the outer cover, which can simplify the manufacturing steps of the absorbent article.

A first aspect of a method of manufacturing a disposable absorbent article according to the present invention is directed to a method of manufacturing a disposable absorbent article having an outer cover and an absorbent member attached to the skin facing side of the outer cover, the absorbent member including an absorber. The method comprises the steps of: a) softening at least a portion of a continuous material to be a crotch zone of the outer cover while transporting the continuous material in its longitudinal direction, the continuous member being a series of material for forming the outer cover and extending continuously in a lateral direction of the absorbent article; b) attaching the absorbent member to the continuous material; and c) cutting the continuous material, with the absorbent member attached thereto, into products.

The absorbent article can be manufactured at least with the crotch zone of the outer cover improved in flexibility by the softening process.

In a second aspect of the method of manufacturing a disposable absorbent article, in the method according to the first aspect, an elastic member is attached from along leg-side edges of the outer cover surrounding the wearer's left and right legs to the crotch zone. The method further comprises the step of d) attaching the elastic members continuously to the continuous material while transporting the continuous material in the longitudinal direction. In the step a), blades of a cutter are applied to at least a portion of the continuous material to be the crotch zone of the outer cover to thereby soften the portion, and part of the elastic members positioned in the portion is cut short to be weakened.

The absorbent article is capable of preventing the absorber from receiving an unnecessary force caused by the contractive forces of the elastic members and degrading in its absorptive function.

Further, the elastic members are attached continuously from along the left and right leg-side edges of the outer cover to the crotch zone, and part of the elastic members positioned in the crotch zone is weakened along with the softening process performed on the crotch zone of the outer cover, which can simplify the manufacturing steps of the absorbent article.

These and other objects, features, aspects and advantages of the present invention will become more apparent from the following detailed description and accompanying drawings.

DESCRIPTION OF THE PREFERRED EMBODIMENTS

Hereinafter, a disposable absorbent article according to an embodiment of the present invention and a method of manufacturing the same will be described.

Figure 1:
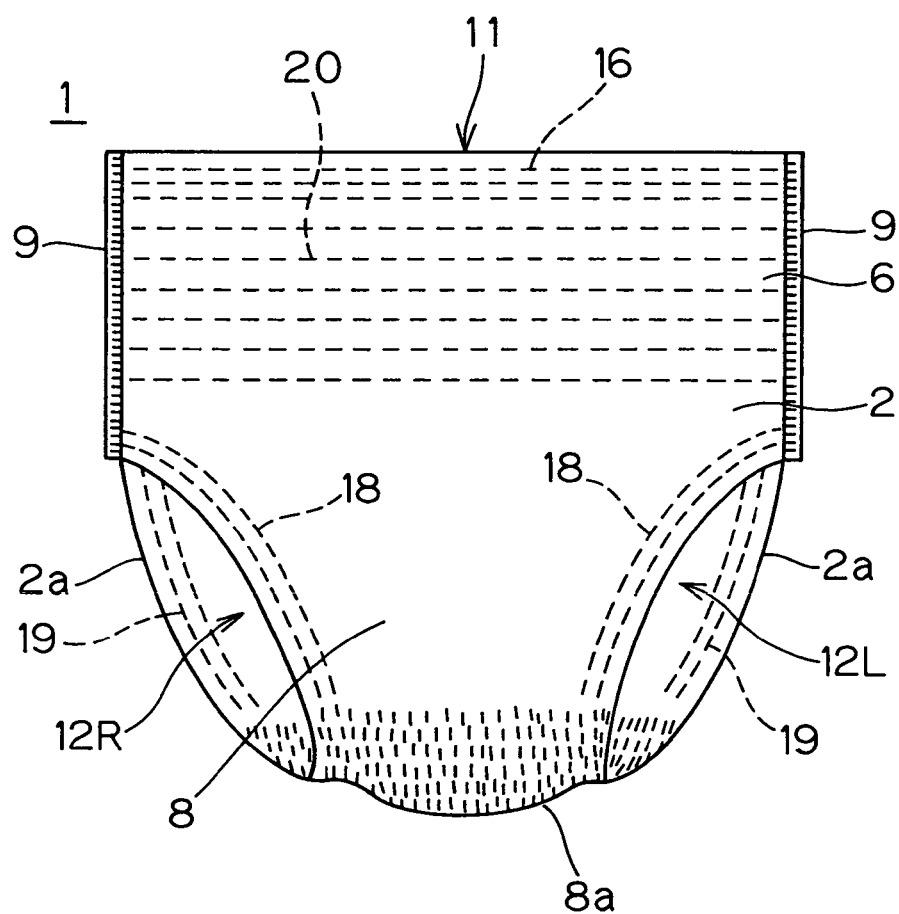
FIG. 1 is a front view of a disposable absorbent article according to an embodiment of the present invention.
Figure 2:
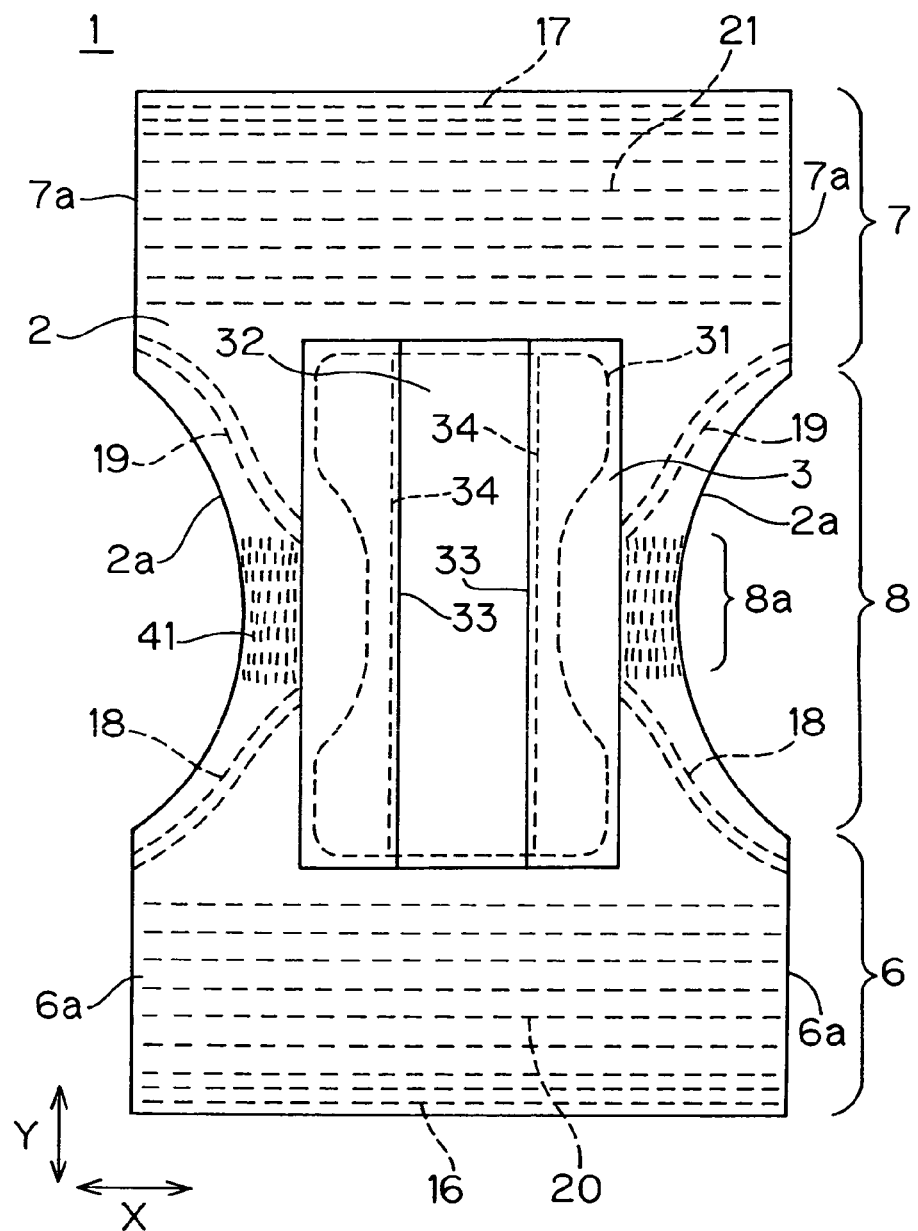
FIG. 2 is a diagram in which the disposable absorbent article shown in FIG. 1 is developed by breaking left and right side bonded parts.

FIG. 1 is a front view of a disposable absorbent article (hereinafter briefly referred to as an "absorbent article") according to an embodiment of the present invention, and FIG. 2 is a diagram in which the disposable absorbent article shown in FIG. 1 is developed by breaking left and right side bonded parts. Throughout the present specification, the front, back, left and right are mentioned relative to a wearer. For example, the wearer's left hand side is called left, and the right hand side is called right. The longitudinal direction Y (cf. FIG. 2) of an absorbent article 1 corresponds to the top-to-bottom or front-to-rear direction of the absorbent article 1, and the lateral direction X (cf. FIG. 2) of the absorbent article 1 corresponds to the side-to-side direction of the absorbent article 1.

As shown in FIGS. 1 and 2, this absorbent article 1 includes an outer cover 2 provided on the exterior side of the absorbent article 1 and an absorbent member 3 bonded to the skin facing side of the outer cover 2.

The outer cover 2 has a front waist region 6, a rear waist region 7 and a crotch region 8 to be applied to the wearer's front waist region, rear waist region and crotch region, respectively. Herein, the outer cover 2 is of a single-piece design integrally formed of the front waist region 6, crotch region 8 and rear waist region 7, by way of example, but may be formed of the front portion and rear portion separated at the crotch region.

Left and right edges 6a of the front waist region 6 and left and right edges 7a of the rear waist region 7 of the outer cover 2 are bonded by predetermined adhesion means while facing each other, so that left and right side bonded parts 9 are formed. Accordingly, the absorbent article 1 is in the pant-type structure having a waist opening 11, and left and right leg openings 12L and 12R. The bonding at these side bonded parts 9 is achieved by adhesion means of one of ultrasonic welding, heating welding, an adhesive (e.g., a hot melt adhesive) and the like, or by combining some of them.

The absorbent member 3 is bonded by adhesion means such as an adhesive (e.g., a hot melt adhesive) to an area of the outer cover 2 on the skin facing side that substantially corresponds to the crotch region 8.

A waist elastic member 16 is attached in a stretched state to the upper edge of the front waist region 6 of the outer cover 2 to extend along the upper edge. A waist elastic member 17 is attached in a stretched state to the upper edge of the rear waist region 7 to extend along the upper edge. Leg elastic members 18 and 19 are attached in a stretched state to left and right leg-side edges 2a of the crotch region 8 forming the leg openings 12L and 12R to extend along these edges. A body elastic member 20 is attached in a stretched state in the lateral direction X to an area of the front waist region 6 around the wearer's torso (an intermediate part of the front waist region 6 in the longitudinal direction Y). A body elastic member 21 is attached in a stretched state in the lateral direction X to an area of the rear waist region 7 around the wearer's torso (an intermediate part of the rear waist region 7 in the longitudinal direction Y).

The outer cover 2 is formed by sandwiching the elastic members 16 to 21 between two sheet members 26 and 27 (cf. FIG. 5B) made of nonwoven fabric. The bonding of the sheet members 26 and 27 to each other and bonding of the elastic members 16 to 21 to the sheet members 26 and 27 are achieved by using adhesion means such as an adhesive (e.g., hot melt adhesive), heating welding, ultrasonic welding or the like.

The absorbent member 3 is formed of an absorbent body 32 including an absorber 31 for absorbing bodily exudates of a wearer, and left and right flaps 33 provided on the absorbent body 32. The absorbent body 32 is formed by sandwiching the absorber 31 between a water repellent or liquid impermeable backsheet and a liquid permeable top sheet not shown. Flap elastic members 34 are attached in a stretched state to free ends of the flaps 33, and the contractive force of the elastic members 34 raises the flaps 33 so that the flaps 33 fit the wearer's skin.

In the absorbent article 1 according to the present embodiment, a crotch zone 8a in the crotch region 8 of the outer cover 2 to be applied to the wearer's crotch is subjected to a softening process. This improves the flexibility of the crotch zone 8a of the outer cover 2, which prevents the crotch zone 8a from being less likely to fit the wearer's body and causing rough and uncomfortable feeling to the wearer's skin.

More specifically, the softening process creates a plurality of almost slit-like holes 41 in the crotch zone 8a of the outer cover 2 which extend through the sheet members 26 and 27 constituting the outer cover 2, thereby making the material flexible. This effectively ensures the flexibility and achieves a high degree of breathability, thereby avoiding dampness. The holes 41 may be arranged in any pattern, and are herein arranged in a staggered pattern to be displaced from each other between adjacent rows of holes 41.

In this absorbent article 1, the leg elastic members 18 and 19 are attached continuously from along the left and right leg-side edges 2a of the outer cover 2 to the crotch zone 8a, and part of the leg elastic members 18 and 19 positioned in the crotch zone 8a is cut short to be weakened. Part of the leg elastic members 18 and 19 positioned in the crotch zone 8a is weakened in this manner, which prevents the absorber 31 from receiving an unnecessary force caused by the contractive forces of the leg elastic members 18 and 19 and degrading in its absorptive function. It should be noted that such structure also achieves advantages in manufacturing steps (which will be described later).

The method of manufacturing the absorbent article 1 will now be described with reference to FIGS. 3, 4, 5A and 5B.

Figure 3:
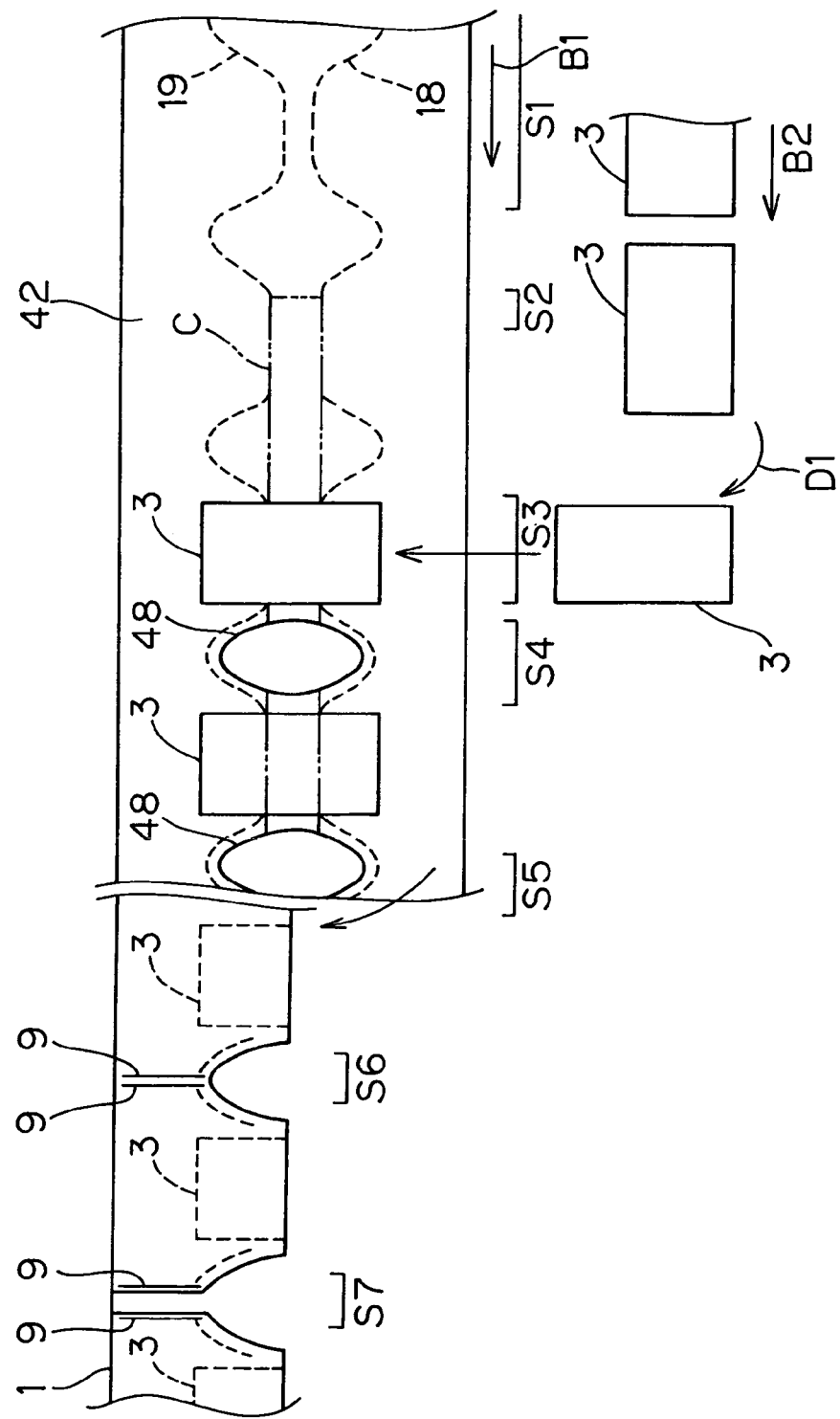
FIG. 3 is a diagram showing manufacturing steps of the disposable absorbent article shown in FIG. 1.

The method includes the following steps as shown in FIG. 3:

S1) outer-cover continuous-material preparing step;
S2) softening step;
S3) absorbent-member attaching step;
S4) leg-hole forming step;
S5) folding step;
S6) side bonding step; and
S7) product separating step.

The steps S1 to S7 are carried out substantially in the order listed above, however, the leg-hole forming step S4 may be carried out prior to the absorbent-member attaching step S3. In FIG. 3, for ease of illustration, the leg elastic members 18 and 19 are each indicated simply by one dashed line, and other elastic members 16, 17, 30 and 31 are omitted from illustration.

As shown in FIG. 3, steps S1 to S7 are carried out while transporting an outer-cover continuous material 42 for forming the outer cover 2 and the like in a transport direction B1 in the longitudinal direction of the outer-cover continuous material 42. In step S1, the outer-cover continuous material 42 for forming the outer cover 2 is prepared. This outer-cover continuous material 42 is a series of material for forming the outer cover 2 extending continuously in the lateral direction X of the absorbent article 1, and includes the elastic members 16, 17, 30 and 31 extending continuously and sandwiched between continuous materials for the sheet members 26 and 27. At this time, the leg elastic members 18 and 19, for example, are attached windingly along lines to be the leg-side edges 2a and each portion to be crotch zone 8a of the outer-cover continuous material 42. Step S1 corresponds to the step of attaching the elastic member according to the present invention.

Figure 4:
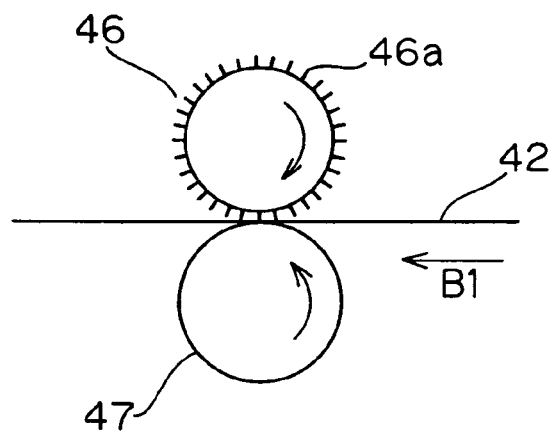
FIG. 4 is a diagram showing a softening step in the manufacturing steps shown in FIG. 3.
Figure 5A:
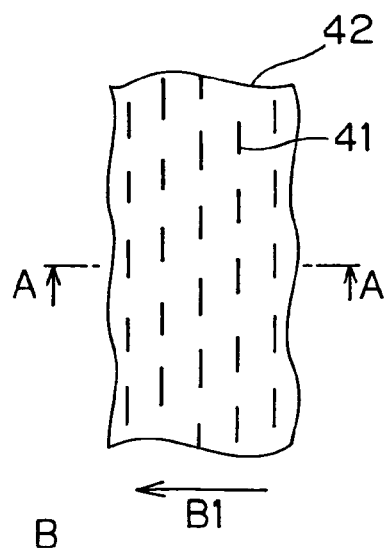
FIG. 5A is an enlarged view of a surface of an outer cover having been subjected to the softening step.
Figure 5B:
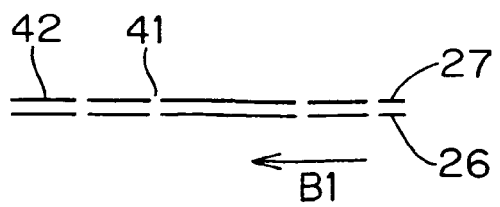
FIG. 5B is a sectional view taken along the line A-A in FIG. 5A.

In the next step S2, each portion to be the crotch zone 8a of the outer-cover continuous material 42 is subjected to a softening process. The softening process is carried out by passing each portion to be the crotch zone 8a of the outer-cover continuous material 42 between a blade roller 46 serving as a cutter and an anvil roller 47, as shown in FIG. 4. The blade roller 46 is provided with a plurality of blades 46a on its outer edge, and the blades 46a are applied to the outer-cover continuous material 42 with the passage of the outer-cover continuous material 42. As a result, as shown in FIGS. 5A and 5B, the plurality of slit-like holes 41 are created in each portion (region surrounded by two-dot chain line in FIG. 3) to be the crotch zone 8a of the outer-cover continuous material 42, so that the portion is softened.

With this softening process, the leg elastic members 18 and 19 attached to each portion to be the crotch zone 8a of the outer-cover continuous material 42 are cut short by the blades 46a of the blade roller 46 to be weakened. In this manner, attaching the leg elastic members 18 and 19 continuously to the outer-cover continuous material 42 and weakening part of the leg elastic members 18 and 19 positioned in each portion to be the crotch zone 8a with the softening process can simplify the manufacturing steps of the absorbent article 1.

Further, in the present embodiment, the blades 46a of the blade roller 46 are arranged to perpendicularly cross the transport direction B1 of the outer-cover continuous material 42. Accordingly, the holes 41 created by these blades 46a extend like slits in the direction perpendicular to the transport direction B1 (vertical direction Y of the absorbent article 1). Furthermore, the arrangement of the blades 46a of the blade roller 46 in such direction allows the leg elastic members 18 and 19 attached substantially in the transport direction B1 to be cut short appropriately and easily by the blades 46a.

In the next step S3, each absorbent member 3 transported in a transport direction B2 substantially in parallel to the transport direction B1 of the outer-cover continuous material 42 is turned at 90 degrees as indicated by an arrow D1, and is attached to each portion to be the crotch zone 8a of the outer-cover continuous material 42.

In the next step S4, the leg holes 48 are formed in the outer-cover continuous material 42 in portions to be the leg-side edges 2a for forming the leg openings 12L and 12R.

In the next step S5, the outer-cover continuous material 42 is folded such that its front portion and rear portion overlap each other. At this time, each absorbent member 3 is sandwiched therebetween.

In the next step S6, portions of the folded outer-cover continuous material 42 to be the side bonded parts 9 of each absorbent article 1 are bonded by the aforementioned adhesion means such as ultrasonic welding, so that the side bonded parts 9 are formed.

In the next step S7, each finished absorbent article 1 is cut into product and separated from each other.

In the above-described absorbent article 1, the softening process is carried out only on the crotch zone 8a of the outer cover 2, however, portions other than the crotch zone 8a may also be subjected to the softening process.

While the above-described absorbent article 1 is in the pant-type structure, the technique according to the present embodiment may also be applied to a hook-and-loop-type disposable diaper or a disposable absorbent article for combined use as pants and a diaper. Such disposable absorbent article for combined use as pants and a diaper represents an article having breaking parts for breaking the article into sections around the waist region and fastening members for re-fastening after breaking, which presents the pant-type structure when the breaking parts are not broken, and presents the hook-and-loop-type structure when the breaking parts are broken.

While the invention has been shown and described in detail, the foregoing description is in all aspects illustrative and not restrictive. It is therefore understood that numerous modifications and variations can be devised without departing from the scope of the invention.

What is claimed is:

1. A method of manufacturing a disposable absorbent article having a crotch zone extending an entirety of the absorbent article in a lateral direction from a first leg-side edge for surrounding a wearer's first leg and a second leg-side edge surrounding the wearer's second leg, the absorbent article having an outer cover and an absorbent member attached to a skin facing side of said outer cover, said absorbent member including an absorber, the absorbent article having elastic members attached from along the leg-side edges of said outer cover surrounding a wearer's left and right legs across the crotch zone, said method comprising the steps of:

softening a continuous material to become said crotch zone of said outer cover while transporting said continuous material in its longitudinal direction, said continuous material being a series of material for fanning said outer cover and extending continuously in a lateral direction of said absorbent article;

attaching said absorbent member to said continuous material;

cutting said continuous material, with said absorbent member attached thereto, into products; and attaching said elastic members continuously to said continuous material while transporting said continuous material in said longitudinal direction; and wherein said softening comprises applying blades of a cutter to said continuous material to become the crotch zone of said outer cover to thereby soften said continuous material, wherein parts of said elastic members positioned in said crotch zone are cut short so as to be weakened, and wherein all of the continuous material that is to become the crotch zone is passed between a blade roller serving as the cutter and an anvil roller so that a plurality of slit-like holes is formed in the continuous material laterally across an entirety of the crotch zone.

2. The method of manufacturing of claim 1, wherein the blade roller creating the slit-like holes has a plurality of blades distributed along an entire circumference of the blade roller.

* * * * *